United States Patent
Hirahara et al.

(10) Patent No.: US 9,505,721 B2
(45) Date of Patent: Nov. 29, 2016

(54) AROMATIC IMIDE COMPOUND AND METHOD FOR PRODUCING SAME

(71) Applicant: AZ ELECTRONIC MATERIALS (LUXEMBOURG) S.A.R.L., Somerville, NJ (US)

(72) Inventors: Eri Hirahara, Shizuoka (JP); Ralph Dammel, Shizuoka (JP); Georg Pawlowski, Shizuoka (JP)

(73) Assignee: AZ ELECRONIC MATERIALS (LUXEMBOURG) S.A.R.L., Luxembourg (LU)

( * ) Notice: Subject to any disclaimer, the term of this patent is extended or adjusted under 35 U.S.C. 154(b) by 0 days.

(21) Appl. No.: 14/439,477

(22) PCT Filed: Oct. 28, 2013

(86) PCT No.: PCT/JP2013/079140
§ 371 (c)(1),
(2) Date: Apr. 29, 2015

(87) PCT Pub. No.: WO2014/073409
PCT Pub. Date: May 15, 2014

(65) Prior Publication Data
US 2015/0299132 A1    Oct. 22, 2015

(30) Foreign Application Priority Data

Nov. 12, 2012 (JP) ................. 2012-248648

(51) Int. Cl.
| | | |
|---|---|---|
| C07D 471/12 | (2006.01) | |
| C07D 221/14 | (2006.01) | |
| C07D 409/06 | (2006.01) | |
| C07D 401/12 | (2006.01) | |
| C07D 403/04 | (2006.01) | |
| C07D 405/04 | (2006.01) | |
| C07D 409/04 | (2006.01) | |
| C07D 409/12 | (2006.01) | |
| G03F 7/004 | (2006.01) | |

(52) U.S. Cl.
CPC ........... *C07D 221/14* (2013.01); *C07D 401/12* (2013.01); *C07D 403/04* (2013.01); *C07D 405/04* (2013.01); *C07D 409/04* (2013.01); *C07D 409/06* (2013.01); *C07D 409/12* (2013.01); *C07D 471/12* (2013.01); *G03F 7/004* (2013.01)

(58) Field of Classification Search
CPC  C07D 221/14; C07D 409/06; C07D 403/04; C07D 401/12; C07D 471/12
USPC ........................................................... 546/98
See application file for complete search history.

(56) References Cited

U.S. PATENT DOCUMENTS

| | | |
|---|---|---|
| 4,371,605 A | 2/1983 | Renner |
| 2003/0064315 A1 | 4/2003 | Choi et al. |
| 2010/0119972 A1 | 5/2010 | Houlihan et al. |
| 2011/0229821 A1 | 9/2011 | Dautel et al. |
| 2012/0289697 A1 | 11/2012 | Murai et al. |

FOREIGN PATENT DOCUMENTS

| | | |
|---|---|---|
| JP | 2004-217748 A | 4/2004 |
| JP | 2012-508911 A | 4/2012 |
| WO | WO 2011/087011 A1 | 7/2011 |

OTHER PUBLICATIONS

Caplus English Abstract DN 1976:592428, 1976, Zhurnal Organicheskoi Khimii, Plakidan V. L. et al.*
Lorenz Steidl et al., "Non-ionic photo-acid generators for applications in two-photon lithography", J. Mater. Chem. vol. 19, pp. 505-pp. 513 (2009).

* cited by examiner

*Primary Examiner* — Rita Desai
(74) *Attorney, Agent, or Firm* — Mitchell Brustein (57) ABSTRACT

[Problem] to provide an aromatic imide compound wherein the sensitivity for visible light such as g-line, h-line etc. is increased and solubility is also improved.
[Means for solving problem] The aromatic imide compound of the invention is a compound represented by the formula (1) below (in the formula, $R^1$ represents a haloalkyl group having 1 to 7 carbon atoms or a haloaryl group, $R^2$ represents a group containing a substituted or unsubstituted, aliphatic or aromatic group which may have a heteroatom, and adjacent $R^2$s may form an imido group by connecting each other, $R^3$ represent a halogen atom or a hydrocarbon group, m is zero or an integer of 1 or more, n is zero or an integer of 1 or more, and a sum of n and m is 1 to 6). These compounds are obtained by following processes. A halogenated naphtharic anhydride is reacted with an aromatic group-containing hydrocarbon such as ethynylbenzene to prepare a naphthalic anhydride substituted by an aromatic group-containing group. The obtained compound is then reacted with hydroxylamine hydrochloride to be made N-hydoxyimidization. Finally, the resultant compound is reacted with a sulfonyl halide such as trifluoromethylsulfonyl chloride to obtain the objective compound.

15 Claims, 3 Drawing Sheets

AROMATIC IMIDE COMPOUND AND METHOD FOR PRODUCING SAME

This application is a United States National Stage Patent Application under 35 U.S.C. §371 of International Patent Application No. PCT/JP2013/079140, filed Oct. 28, 2013, which claims priority to Japanese Patent Application No. 2012-248548, filed Nov. 12, 2012, the contents of which are being hereby incorporated herein by reference.

TECHNICAL FIELD

The present invention relates to an aromatic imide compound and a method for preparing the same.

BACKGROUND ART

It is expected that an acid generator for a photoresist material has a molecular structure which can absorb ultraviolet rays or light having bigger energy than ultraviolet rays and has a bond which can generate an acid after excitation due to the light absorption. As such acid generators, onium salt compounds, oxime compounds, amide compounds, imide compounds, and the like are known. For example, sulfonic esters, the aromatic part of which is unsubstituted, are known as the imide compounds (see the patent document 1 below, for example).

CITATION LIST

Patent Document

Patent document 1: U.S. Pat. No. 4,371,605 B

DISCLOSURE OF THE INVENTION

Problems to be Solved by the Invention

There, however, is still a problem like that the conventionally known acid generators described in the patent document 1 etc. cannot absorb long wavelength light efficiently.

Accordingly, the present invention was made to solve the aforementioned problem. An object of the present invention is to provide a new aromatic imide compound which can generate an acid when the compound absorbs long wavelength light. Further, another object of the present invention is to provide a method for preparing the aromatic imide compound easily and at a high yield.

Means for Solving the Problems

The present invention relates to an aromatic imide compound described in items [1] and [2] below, and a method for preparing an aromatic imide compound described in items [3] and [4] below.

[1] An aromatic imide compound represented by the formula (1):

(1)

in which $R^1$ represents a haloalkyl group having 1 to 7 carbon atoms or a haloaryl group, $R^2$ represents a group containing a substituted or unsubstituted, aliphatic or aromatic group which may have a heteroatom, adjacent $R^2$s may form an imido group by connecting each other, $R^3$ represents a halogen atom or a hydrocarbon group, m is zero or an integer of 1 or more, n is zero or an integer of 1 or more, and a sum of n and m is 1 to 6.

[2] The aromatic compound described in the item [1], which can absorb light of g-line (436 nm) and/or h-line (405 nm).

[3] A method for preparing an aromatic imide compound represented by the formula (1):

(1)

in which $R^1$ represents a haloalkyl group having 1 to 7 carbon atoms or a haloaryl group, $R^2$ represents a group containing a substituted or unsubstituted, aliphatic or aromatic group which may have a heteroatom, adjacent $R^2$s may form an imido group by connecting each other, $R^3$ represents a halogen atom or a hydrocarbon group, m is zero or an integer of 1 or more, n is zero or an integer of 1 or more, and a sum of n and m is 1 to 6, wherein the method for preparing an aromatic amide compound comprises, (A) a first step preparing compounds represented by the formula (4-1) and/or the formula (4-2):

(4-1)

(4-2)

in which $Z^1$ and $Z^2$ each independently represent a hydroxyl group or an alkoxy group and $R^2$, $R^3$, m, and n each represent the same meanings as those identified above, by reacting compounds represented by the formula (3-1) and/or the formula (3-2):

(3-1)

(3-2)

in which X represents a halogen atom and $R^3$, $Z^1$, $Z^2$, m, and n each represent the same meanings as those identified above, with a hydrocarbon compound containing a substituted or unsubstituted, aliphatic or aromatic group which may have a heteroatom, (B) a second step preparing a compound represented by the formula (5):

(5)

in which $R^2$, $R^3$, m, and n each represent the same meanings as those identified above, by reacting the compounds represented by the formula (4-1) and/or the formula (4-2) with a hydroxylammonium compound, and (C) a third step preparing the aromatic amide compounds represented by the formula (1) by reacting the compound represented by the formula (5) with a compound represented by the formula (6):

$R^1SO_2Y$ (6)

in which Y represents a halogen atom or a tosyl group and $R^1$ represent the same meanings as those identified above.

[4] The method for preparing an aromatic imide compound described in the item [3], wherein the aromatic amide compound represented by the formula (1) is a compound which can absorb light of g-line (436 nm) and/or h-line (405 nm).

Advantageous Effect of the Invention

The aromatic imide compound of the invention can generate an acid when the compound absorbs light of long wavelength side. The method for preparing an aromatic imide compound of the invention can be easily conducted and the objective compounds can be obtained at a high yield by the method for preparing an aromatic imide compound of the invention

MODE FOR CARRYING OUT THE INVENTION

The present invention will be explained below in detail.

The aromatic imide compound of the invention is represented by the formula (1) below. The aromatic imide compound of the invention can generate an acid when the compound absorbs light of long wavelength side. In addition, the aromatic imide compound of the invention has specific characteristics such as an improved heat resistance when used as a photoacid generator and an easy synthesis thereof and further has an improved sensitivity for visible light such as g-line and h-line and an improved solubility as compared with known photoacid generators. The aromatic imide compound of the invention, therefore, can be used suitably as a photoacid generator.

(1)

In which $R^1$, $R^2$, $R^3$, m, and n each represent the same meanings as those identified above.

As the aromatic imide compound of the invention, one which can absorb light having wavelengths of 380 nm to 830 nm as light of long wavelength side, especially absorb g-line (436 nm) and/or h-line (405 nm) efficiently is preferred generally. It can be confirmed by the ultraviolet and visible absorption spectrometry whether the compound absorbs these lights or not. Furthermore, it can be confirmed by a method described in Example (Evaluation test of acid generating ability) whether the compound can generate an acid or not.

The aromatic imide compound of the invention can also absorb light of shorter wavelength than 380 nm as light of short wavelength side, and among them, compounds which can absorb i-line (365 nm) efficiently are preferred.

$R^1$ in the formula (1) represents a haloalkyl group having 1 to 7 carbon atoms or a haloaryl group, wherein a part or all of hydrogen atoms in an alkyl group having 1 to 7 carbon atoms or an aryl group are substituted by halogen atoms.

Examples of the halogen atom include a fluorine atom, a chlorine atom, a bromine atom, and an iodine atom. Furthermore, as the alkyl group having 1 to 7 carbon atoms, there are exemplified linear, branched and cyclic alkyl groups, and examples of the alkyl group include specifically, but are not limited to, a methyl group, an ethyl group, a propyl group, a butyl group, a pentyl group, a hexyl group, or a heptyl group. Examples of the aryl group include a phenyl group and a tolyl group.

$R^2$ in the formula (1) represents a group containing a substituted or unsubstituted, aliphatic or aromatic group which may contain a hetero atom. Specific examples of the aromatic group include, but are not limited to, a biphenyl group, a trityl group, a styryl group, a diphenylvinyl group, a phenylethynyl group, a naphthyl group, a fluorenyl group, an anthracenyl group, a phenanthryl group, and the like. Specific examples of the aromatic group containing a hetero atom include, but are not limited to, functional groups formed from following compounds.

The $R^2$ may be represented as a group $R^4$-$R^5$—. In the group, $R^4$ represents the aforementioned substituted or unsubstituted, aliphatic or aromatic group or a substituted or unsubstituted, aliphatic or aromatic group containing a heteroatom. Further, $R^5$ represents a direct bond or a divalent group. Specific examples of the divalent group include, but are not limited to, an alkylene group, an alkenylene group, an alkynylene group, an ether group, an ester group, a thioester group, a sulfonic ester group, a boronic ester group, a sulfide group, a disulfide group, an amino group, an amido group, a thioamido group, diimido group, an azo group, a diazo group, a triazole group, and so on, which may be substituted or unsubstituted.

Examples of the alkylene group include, but are not limited to, a methylene group, an methyleneoxymethylene group, a fluoromethylene group, an ethylene group, a propylene group, a tetramethylene group, and so on.

Examples of the alkenylene group include, but are not limited to, a vinylene group, a 1-methylvinylene group, a propenylene group, a 1-butenylene group, a 2-butenylene group, a 1-pentenylene group, 2-pentenylene group, and so on.

Examples of the alkynylene group include, but are not limited to, an ethynylene group, a propenylene group, a butanylene group, and so on.

In addition, when $R^4$ or $R^5$ is substituted, as the substituent, there are exemplified, but are not limited to, a halogen atom, an alkyl group, a haloalkyl group, an alkoxy group and a haloalkoxy group, which have 1 to 10 carbon atoms, and an aryl or aryloxy group which may be substituted or unsubstituted.

Examples of the halogen atom as the aforementioned substituent include, but are not limited to, a fluorine atom, a chlorine atom, a bromine atom, and an iodine atom. Furthermore, specific examples of the alkyl and haloalkyl groups having 1 to 10 carbon atoms include, but are not limited to, a methyl group, an ethyl group, a n-propyl group, an i-propyl group, a n-butyl group, an i-butyl group, a s-butyl group, a t-butyl group, a n-amyl group, an i-amyl group, a s-amyl group, a n-hexyl group, a n-heptyl group, a n-octyl group, n-nonyl group, a n-decyl group, a trifluoromethyl group, a pentafluoroethyl group, and so on. Specific examples of the alkoxy and haloalkoxy groups having 1 to 10 carbon atoms include, but are not limited to, a methoxy group, an ethoxy group, a n-propoxy group, an i-propoxy group, a n-butoxy group, a n-amyloxy group, a n-octyloxy group, a n-decyloxy group, a trifluoromethoxy group, a pentafluoroethoxy group, and so on. Specific examples of the substituted or unsubstituted aryl or aryloxy groups include, but are not limited to, a phenyl group, a naphthyl group, a phenoxy group, and so on.

Examples of the substituted or unsubstituted phenyl group which is a specific example of the substituted or unsubstituted aromatic groups of $R^2$ or $R^4$ include, but are not limited to, a phenyl group, an o-tolyl group, a m-tolyl group, a p-tolyl group, an o-ethylphenyl group, a m-ethylphenyl group, a p-ethylphenyl group, a p-(n-propyl)phenyl group, a p-(i-propyl)phenyl group, a p-(n-butyl)phenyl group, a p-(i-butyl)phenyl group, a p-(s-butyl)phenyl group, a p-(t-butyl) phenyl group, a p-(n-amyl)phenyl group, a p-(i-amyl)phenyl group, a p-(t-amyl)phenyl group, an o-methoxyphenyl group, a m-methoxyphenyl group, a p-methoxyphenyl group, an o-ethoxyphenyl group, a m-ethoxyphenyl group, a p-ethoxyphenyl group, a p-(n-propoxy)phenyl group, a p-(i-propoxy)phenyl group, a p-(n-butoxy)phenyl group, a p-(i-butoxy)phenyl group, a p-(s-butoxy)phenyl group, a p-(t-butoxy)phenyl group, a p-(n-amyloxy)phenyl group, a p-(i-amyloxy)phenyl group, a p-(t-amyloxy)phenyl group, a p-chlorophenyl group, a p-bromophenyl group, a p-fluorophenyl group, a 2,4-dichlorophenyl group, a 2,4-dibromophenyl group, a 2,4-difluorophenyl group, a 2,4,6-trichlorophenyl group, a 2,4,6-tribromophenyl group, a 2,4,6-trifluorophenyl group, a pentachlorophenyl group, a pentabromophenyl group, a pentafluorophenyl group, a p-biphenylyl group, and so on.

Examples of the aforementioned substituted or unsubstituted naphthyl group include, but are not limited to, a naphthyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, a 8-methyl-2-naphthyl group, and so on. These substituted or unsubstituted phenyl and naphthyl groups also correspond to examples of the substituted or unsubstituted aromatic group which are substituents of the aromatic group in $R^2$ or $R^4$.

Examples of the halogen atom in $R^3$ of the formula (1) include a fluorine atom, a chlorine atom, a bromine atom, and an iodine atom. Examples of the hydrocarbon group in $R^3$ include an alkyl group, a haloalkyl group, a substituted or unsubstituted aromatic hydrocarbon group which may contain a hetero atom, and so on, which are described above as a substituent.

Specific examples of the aromatic imide compounds represented by the formula (1) include, as compounds which function as an acid generator having high sensitivity and high efficiency for actinic light used for exposure, in particular g-line (436 nm) and h-line (405 nm) and also having high solubility for generic organic solvents, aromatic imide compounds represented by the formula (2):

(2)

in which $R^1$ and $R^4$ represent the same meanings as those defined above.

As the substituted or unsubstituted aromatic group, which may contain a hetero atom, in $R^4$ of the formula (2), there are preferred, but are not limited to, a phenyl group, a naphthyl group, an anthracenyl group, a fluorophenyl group, a methylphenyl group, a methoxyphenyl group, a phenoxyphenyl group, a pyridyl group, a thienyl group, and so on from the view point of synthesis.

Specific examples of the aromatic imide compounds represented by the formula (1) include, but are not limited to, compounds represented by the chemical formulae below.

-continued

[Preparation Method of Aromatic Imide Compound]

As the method for preparing the aromatic imide compound of the invention consists of relatively few steps and the reaction in each step is simple and the purification of the compound obtained in each step can be conducted relatively easily, the method of the invention becomes easy and high efficient preparation method. That is, the method for preparing an aromatic imide compound of the invention is a method for preparing an aromatic imide compound represented by the formula (1) above and comprises;

(A) a first step preparing compounds represented by the formulae (4-1) and/or (4-2) below by reacting the compounds represented by the formulae (3-1) and/or (3-2) with a substituted or unsubstituted, aromatic group-containing hydrocarbon which may contain a hetero atom, (3-1)

(3-2)

in which m, n, X, $R^3$, $Z^1$ and $Z^2$ represent the same meanings as those defined above, (4-1)

(4-2)

in which m, n, $R^2$, $R^3$, $Z^1$ and $Z^2$ represent the same meanings as those defined above, (B) a second step preparing a compound represented by the formula (5) below by reacting compounds represented by the formulae (4-1) and/or (4-2) with a hydroxylammonium compound, (5)

in which m, n, $R^2$, and $R^3$ represent the same meanings as those defined above, (C) a third step preparing the compound represented by the formula (1) above by reacting the compound represented by the formula (5) with a compound represented by the formula (6);

$$R^1SO_2Y \qquad (6)$$

in which $R^1$ and Y represent the same meanings as those defined above.

The compound represented by the formula (3-1) represents a dicarboxylic acid compound when both of $Z^1$ and $Z^2$ are hydroxyl groups, and represents a diester compound when both of $Z^1$ and $Z^2$ are alkoxy groups which may have a substituent, and represents a monocarboxylic acid monoester compound when one is a hydroxyl group and the other is an alkoxy group which may have a substituent.

The compound represented by the formula (3-2) has a structure of cyclic acid-anhydride and it may cause an intramolecular ring-opening in the reaction system under some conditions after starting of the first step. At that time, as a salt of the compound represented by the formula (3-1) can be formed in the reaction system, the reaction of the first step proceeds as like when the reactant is the compound represented by the formula (3-1).

The compound represented by the formula (4-1) also represents a dicarboxylic acid compound when both of $Z^1$ and $Z^2$ are hydroxyl groups, a diester compound when both of $Z^1$ and $Z^2$ are alkoxy groups which may have a substituent, and a monocarboxylic acid monoester compound when one is a hydroxyl group and the other is an alkoxy group which may have a substituent.

The compound represented by the formula (4-2) has a structure of cyclic acid-anhydride but it may cause an intramolecular ring-opening in the reaction system after starting of the reaction. At that time, as a salt of the compound represented by the formula (4-1) can be formed in the reaction system, the reaction of the second step proceeds as like when the reactant is the compound represented by the formula (4-1).

In the $Z^1$ and $Z^2$, as the alkoxy group which may have a substituent, there are preferred, but are not limited to, a methoxy group, an ethoxy group, a propoxy group, an iso-propoxy group or a tert-butoxy group from the view point of the synthesis.

In the formulae (3-1) and (3-2), there are exemplified a fluorine atom, a chlorine atom, a bromine atom, and an iodine atom as the halogen atom of X. In addition, there are exemplified hydrocarbons which may have a hydroxyl group, a mercapto group, an amino group, a carbonyl group, a carboxyl group, an acyl group, an amido group, an imino group, an azo group, a nitro group, a cyano group, a sulfo group, a phosphido group or the like as the hydrocarbon used for the reaction with X, a carbon atom of which may be substituted by a hetero atom.

In the formula (6), there are exemplified a fluorine atom, a chlorine atom, a bromine atom, and an iodine atom as the halogen atom of Y.

[First Step]

The first step is a step preparing compounds represented by the formula (4-1) and/or the formula (4-2) by reacting compounds represented by the formula (3-1) and/or formula (3-2) with a substituted or unsubstituted, aliphatic group- or aromatic group-containing hydrocarbon which may contain a hetero atom.

A coupling reaction, addition reaction, thioetherification reaction, a condensation reaction or the like is conducted in the first step according to the purpose.

If the coupling reaction or addition reaction is conducted in the first step, compounds represented by the formula (3-1) and/or the formula (3-2) are reacted with a functional group of an aliphatic or aromatic hydrocarbon to construct a carbon-carbon bond, compounds represented by the formula (4-1) and/or the formula (4-2) being prepared. However, if the diazo coupling reaction is conducted, a diazo bond is constructed and if a cycloaddition reaction is conducted, a heterocyclic structure is constructed, compounds represented by the formula (4-1) and/or the formula (4-2) being prepared. Further, if the thioetherification reaction is conducted, compounds represented by the formula (3-1) and/or the formula (3-2) are reacted with a functional group of an aromatic group-containing hydrocarbon to construct a sulfide, disulfide bond or the like, compounds represented by the formula (4-1) and/or the formula (4-2) being prepared. Furthermore, if the condensation reaction is conducted, compounds represented by the formula (3-1) and/or the formula (3-2) are reacted with a functional group of an aliphatic group- or aromatic group-containing hydrocarbon to construct an ester bond, a thioester bond, a sulfuric ester bond, a nitric ester bond, a phosphoric ester bond, an amido bond, an imido bond or the like, compounds represented by the formula (4-1) and/or the formula (4-2) being prepared.

The reaction temperature in the first step varies by the kind of the reactions described above but is preferably 25° C. to 60° C. The reaction time thereof is preferably 1 hour to 5 hours. The reaction can be conducted not only in a solvent but also in the absence of solvent. As the solvent, there are specifically used, but are not limited to, aromatic hydrocarbon solvents such as benzene, toluene, xylene, ethylbenzene, and mesitylene; ether solvents such as diethyl ether, n-butyl ether, anisole, diphenyl ether; tetrahydrofuran, dioxane, bis(2-methoxyethyl) ether, and 1,2-bis(2-methoxyethoxy) ethane; halogen-containing solvents such as dichloromethane and chloroform; organic polar solvents such as N-methylpyrrolidone, dimethylformamide, and dimethylacetamide; and mixture thereof. Further, reaction catalysts, inorganic or organic bases, and inorganic or organic acids may be optionally used according to the kind of the aforementioned reactions. Though the reaction pressure may be any one of a reduced pressure, an atmospheric pressure, and an increased pressure, it is preferred that the reaction in increased pressure is conducted by use of a pressure-resistant reaction vessel when the reaction temperature is higher than the boiling point of the solvent used.

Molar ratio of the compounds represented by the formula (3-1) and/or the formula (3-2) and the aromatic group-containing hydrocarbon [molar number of the compounds represented by the formula (3-1) and/or the formula (3-2)/molar number of the aromatic group-containing hydrocarbon] at the start of the reaction is preferably 10/90 to 90/10, more preferably 25/75 to 75/25, and further more preferably 40/60 to 60/40.

Purification and separation methods of the compounds represented by the formula (4-1) and/or the formula (4-2) can be conducted by reprecipitation using one kind of solvents or two kinds of different solvents, but are not limited to this method.

In the first step, as a substituted or unsubstituted, aliphatic and/or aromatic group-containing hydrocarbon which may contain a hetero atom and which react with an X part in the formula (3-1) and/or the formula (3-2), any compounds may be used so far as the compound can form $R^2$ group of the compounds represented by the formula (4-1) and/or the formula (4-2) after the reaction. Examples of the hydrocarbon include, but are not limited to, compounds represented by chemical formulae below.

The first step may be any steps as far as the formula (4-1) and/or the formula (4-2) are formed after the reaction. In the first step, the aptitude for the reaction does not change remarkably by difference of reactants, that is, whether the reactant is a compound represented by the formula (3-1) or a compound represented by the formula (3-2), and is a dicarboxylic acid compound or a dicarboxylic ester compound or a monocarboxylic acid monoester compound when the reactant is a compound represented by the formula (3-1).

Further, even if compounds represented by the formula (3-2) are used as a reactant in the first step, a compound represented by the formula (4-1) may be produced after the reaction. Such product can also be used as a reactant in the second step.

[Second Step]

The second step is a step preparing a compound represented by the formula (5) by reacting compounds represented by the formula (4-1) and/or the formula (4-2) with a hydroxylammonium compound. In the reaction of the second step, a carboxyl part of the compounds represented by the formula (4-1) and/or the formula (4-2) is reacted with the hydroxylammonium compound to prepare the compound represented by the formula (5).

The reaction temperature in the second step is preferably 70° C. to 90° C. The reaction time is preferably 6 hours to 12 hours. The reaction may be conducted in solvent or absence of solvent. As the solvent used in the second step, there are exemplified specifically, but are not limited to, solvents described in the first step. Furthermore, an organic or inorganic base may be used in the second step suitably. Though the reaction pressure may be any one of a reduced pressure, an atmospheric pressure, and an increased pressure, it is preferred that a reaction in increased pressure is conducted by use of a pressure-resistant reaction vessel as a reaction vessel when the temperature of the reaction is higher than the boiling point of the solvent used.

Molar ratio of the compounds represented by the formula (4-1) and/or the formula (4-2) and the hydroxylammonium compound [molar number of the compounds represented by the formula (4-1) and/or the formula (4-2)/molar number of the hydroxylammonium compound] at the start of the reaction is preferably 10/90 to 90/10, more preferably 25/75 to 75/25, and further more preferably 40/60 to 60/40.

Purification and separation methods of the compound represented by the formula (5) can be conducted by reprecipitation using one kind of solvents or two kinds of different solvents, but are not limited to this method.

Specific examples of the hydroxylammonium compound include, but are not limited to, hydroxylammonium chloride, hydroxylammonium sulfate, hydroxylammonium phosphate, hydroxylammonium acetate, hydroxylammonium oxalate, and so on. Furthermore, ammonium salt may be produced in the reaction system by use of a plural reagent, for example, an inorganic acid and hydroxylamine instead of using the hydroxylammonium compound.

The second step may be any steps as far as a compound represented by the formula (5) is formed after the reaction. In the second step, the aptitude for the reaction does not change remarkably by difference of reactants, that is, whether the reactant is a compound represented by the formula (4-1) or a compound represented by the formula (4-2), and is a dicarboxylic acid compound or a dicarboxylic ester compound or a monocarboxylic acid monoester compound when the reactant is a compound represented by the formula (4-1).

[Third Step]

The third step is a step preparing an aromatic imide compound represented by the formula (1) by reacting a compound represented by the formulae (5) with a compound represented by the formulae (6). The reaction of the third step is a condensation reaction and a hydroxyl group of the compound represented by the formula (5) is reacted with a sulfonium halide to prepare the aromatic imide compound represented by the formula (1).

The reaction temperature in the third step is preferably 0° C. to 40° C. The reaction time is preferably 2 hours to 4 hours. Though the reaction pressure may be any one of a reduced pressure, an atmospheric pressure, and an increased pressure, it is preferred that a reaction in increased pressure is conducted by use of a pressure-resistant reaction vessel as a reaction vessel when the temperature of the reaction is higher than the boiling point of the solvent used.

The reaction may be conducted in solvent or absence of solvent. As the solvent used in the third step, there are exemplified specifically, but are not limited to, solvents described in the first step. Furthermore, a reaction catalyst may be used in the third step suitably.

Specific examples of fluoroalkylsulfonic or fluoroarylsulfonic acid halogenides represented by the formula (6) include, but are not limited to, trifluoromethylsulfonyl chloride, pentafluoroethylsulfonyl chloride, heptatluoro-n-propylsulfonyl chloride, heptafluoroisopropylsulfonyl chloride, nonafluoro-n-butylsulfonyl chloride, nonafluoroisobutylsulfonyl chloride, perfluoro-n-pentylsulfonyl chloride, perfluoroisopentylsulfonyl chloride, perfluoro-n-hexylsulfonyl chloride, perfluoroisohexylsulfonyl chloride, perfluoro-n-heptylsulfonyl chloride, perfluoroisoheptylsulfonyl chloride, pentafluorophenylsulfonyl chloride, and so on. Furthermore, a sulfonic anhydride may be used or a sulfonyl chloride compound may be produced in the reaction system by use of a plural reagent, for example, a sulfonic acid and thionyl chloride, instead of the compound represented by the formula (6).

Molar ratio of the compound represented by the formula (5) and the compound represented by the formula (6) [molar number of the compound represented by the formula (5)/molar number of the compound represented by the formula (6)] at the start of the reaction is preferably 10/90 to 90/10, more preferably 25/75 to 75/25, and further more preferably 40/60 to 60/40.

Purification and separation methods of the compounds represented by the formula (1) can be conducted by reprecipitation using one kind of solvents or two kinds of different solvents, but are not limited to this method.

The aromatic imido compound represented by the formula (1) is useful as an acid generator, particularly as a high sensitive and high efficient acid generator for g-line, h-line and actinic light for broadband exposure which contains these g- and h-lines.

EXAMPLE

Hereinafter, the invention will be specifically described with reference to Examples. However, it should be understood that the present invention is not restricted by these Examples by no means.

The measuring devices and measurement conditions of physical properties in examples will be described below.

[1] Mass spectrometry
Machine: LCQ Advantage MAX manufactured by Thermo Fisher Scientific Inc.
Detection method: ESI method
Measurement solvent: Aqueous ammonium acetate solution/acetonitrile
[2] $^1$H NMR
Machine: JNM-EX400 manufactured by JEOL Ltd.
Measurement solvent: CDCl$_3$, Acetone-d6 or DMSO-d6
[3] Ultraviolet and visible absorption spectrum Types of machines: Varian Cary4000 manufactured by Agilent Technologies, Inc.
Measurement solvent: Dichloromethane
[4] Thermal analysis
Machine: EXSTAR6000 TG/DTA6200 manufactured by Seiko Instruments Inc.

Example 1

First step: Synthesis of 4-phenylethynyl-1,8-naphthalic anhydride)

(7)

-continued

(8)

Into a 1 L three-neck flask equipped with stirrer, nitrogen gas inlet tube, and thermometer, 5.0 g (18 mmol) of 4-bromo-1,8-naphthalic anhydride (Compound 7) as a reactant, 2.3 g (23 mmol) of ethynylbenzene, 0.24 g (0.9 mmol) of triphenylphosphine, 0.63 g (0.9 mmol) of bis(triphenylphosphine)paradium (II) dichloride, 0.17 g (0.9 mmol) of copper iodide (I), and 18 ml of triethylamine as a reaction reagent, and 180 mL of dehydrated dimethylformamide as a reaction solvent were charged and stirred at a room temperature for 30 minutes under nitrogen gas inflow. The temperature was increased to 55° C. and the reacted for 2 hours at the temperature. After the end of the reaction, triethylamine and dimethylformamide were distilled out at a reduced pressure. By reprecipitation and drying thereof under reduced pressure, 5.1 g (yield: 95%) of 4-phenylethynyl-1,8-naphthalic anhydride in pale yellow powder form were obtained.

It was identified by analysis of $^1$H NMR and mass spectrometry below that the product obtained was Compound 8. In addition, corresponding hydrogen atoms are represented in italics below.

$^1$H-NMR (400 MHz, DMSO-d6): 7.535-7.508 (3H, m, $C_6H_5$—), 7.818-7.794 (2H, in, $C_6H_5$—), 8.038 (1H, t, J=7.8 Hz, $C_{10}H_5$—), 8.126 (1H, dd, J=7.6, 1.2 Hz, $C_{10}H_5$—), 8.498 (1H, dd, J=7.6, 1.2 Hz, $C_{10}H_5$—), 8.598 (1H, dd, J=7.6, 1.2 Hz, $C_{10}H_5$—), 8.862 (1H, dd, J=8.4, 7.2 Hz, $C_{10}H_5$—) ppm.

Second step: synthesis of N-hydroxy-4-phenylethynyl-1,8-naphthalimide

Into a 500 mL one-neck flask equipped with stirrer, reflux condenser, and thermometer, 3.6 g (12 mmol) of Compound 8 as a reactant, 1.7 g (24 mmol) of hydroxylamine hydrochloride and 3.1 g of sodium bicarbonate as a reaction reagent, and 300 mL of ethanol as a reaction solvent were charged and reacted at 85° C. for 12 hours under reflux. After the end of the reaction, the product was reprecipitated in 1N hydrochloride aqueous solution, separated from the solution by filtration, and washed water, followed by drying under a reduced pressure to obtain 3.5 g (yield: 98%) of N-hydroxy-4-phenylethynyl-1,8-naphthalimide (Compound 9) in pale yellow solid form.

It was identified by analysis of $^1$H NMR and mass spectrometry below that the product obtained was Compound 9. In addition, corresponding hydrogen atoms are represented in italics below.

$^1$H-NMR (400 MHz, DMSO-d6): 7.533-7.499 (3H, m, $C_6H_5$—), 7.795-7.771 (2H, m, $C_6H_5$—), 7.993 (1H, t, J=7.8 Hz, $C_{10}H_5$—), 8.086 (1H, d, J=7.6 Hz, $C_{10}H_5$—), 8.476 (1H, d, J=7.6 Hz, $C_{10}H_5$—), 8.567 (1H, d, J=7.2 Hz, $C_{10}H_5$—), 8.781 (1H, d, J=8.4 Hz, $C_{10}H_5$—), 10.815 (1H, s, OH) ppm.

Third step: synthesis of N-trifluoromethanesulfonyloxy-4-phenylethynyl-1,8-naphthalimide Into a 300 mL three-neck flask equipped with ice bath, stirrer, nitrogen gas inlet tube, and thermometer, 6.8 g (22 mmol) of Compound 9 as a reactant, and 120 mL of dehydrated pyridine as a reaction solvent were charged and dissolved enough at a room temperature under inflow of nitrogen gas. After that, 7.3 g (43 mmol) of trifluoromethanesulfonyl chloride was drop-wise added as a reaction reagent while the reaction temperature was retained at 0° C. with the ice bath. After stirring for 30 minutes, it was cooled down to a room temperature and reacted for 2 hours at this temperature. After the end of the reaction, the product was reprecipitated in pure water, separated the precipitate from the solution by filtration, and dried. The product was reprecipitated with dichloromethane and hexane or ethanol and dried under a reduced pressure to obtain 6.6 g (yield: 69%) of N-trifluoromethanesulfonyloxy-4-phenylethynyl-1,8-naphthalimide (Compound $1_H$) in pale yellow solid form.

It was identified by analysis of $^1$H NMR and mass spectrometry below that the product obtained was Compound $1_H$. In addition, corresponding hydrogen atoms are represented in italics below.

¹H-NMR (400 MHz, CDCl₃): 7.501-7.259 (3H, m, C₆H₅—), 7.714-7.681 (2H, m, C₆H₅—), 7.926 (1H, t, J=8.0 Hz, C₁₀H₅—), 8.025 (1H, d, J=8.0 Hz, C₁₀H₅—), 8.646 (1H, d, J=7.6 Hz, C₁₀H₅—), 8.735 (1H, dd, J=7.2, 0.8 Hz, C₁₀H₅—), 8.879 (1H, dd, J=8.4, 0.8 Hz, C₁₀H₅—) ppm. MS: 463.1 ([M+NH₄]⁺).

Figure 1:
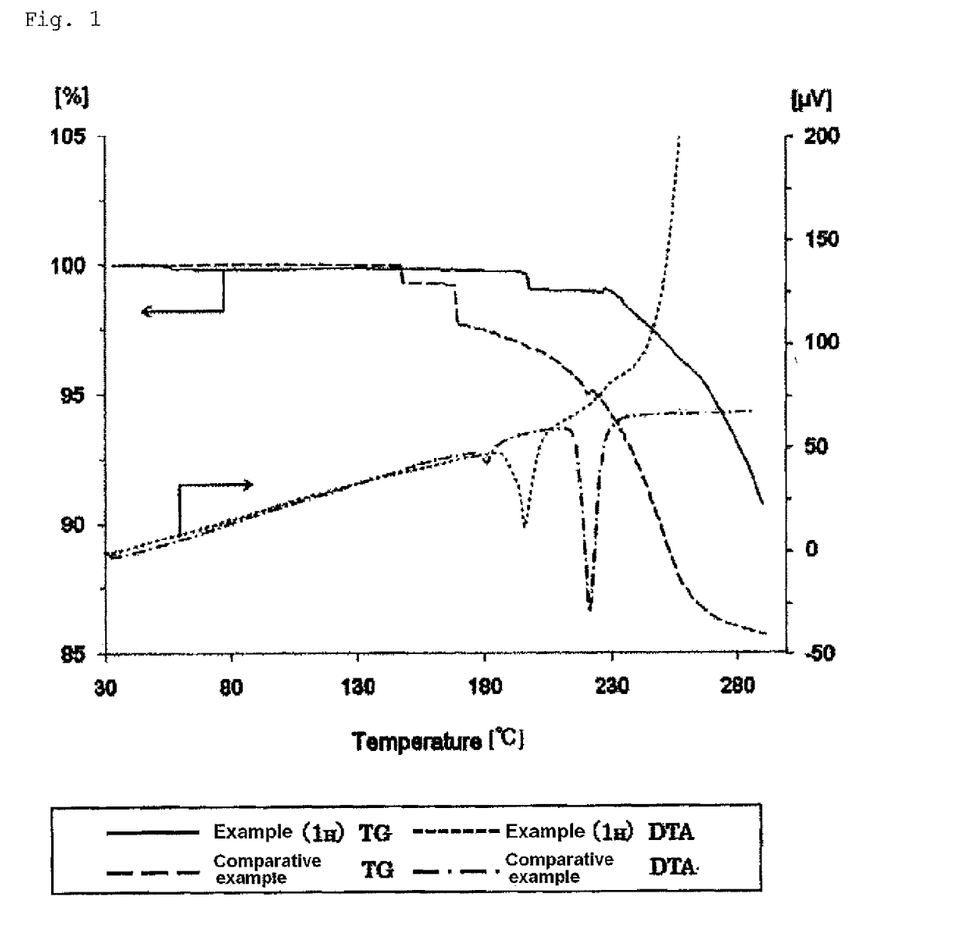
FIG. 1 is a graph showing evaluation results by heat analysis of N-trifluoromethanesulfonyloxy-4-phenylethynyl-1,8-naphthalimide obtained in Example 1.

Heat resistance evaluation of Compound $1_H$ obtained by the example above was conducted by the thermal analysis. The results are shown in FIG. 1. Furthermore, N-trifluoromethanesulfonyloxy-1,8-naphthalimide manufactured by Toyo Gosei CO., Ltd. was used as a comparative example.

Examples 2 to 5

The reaction was conducted as same as in Examples 1 except that reactants, reaction reagents and amounts thereof in the first to third steps in Example 1 were changed to reactants, reaction reagents, and amounts in the first to third steps of Examples 2 to 5 described in Table 1 to obtain products in each step in the amounts and yields described in Table 1. The Compounds $8_F$, $8_{MeO}$, $8_{PhO}$, $8_{Th}$, $9_F$, $9_{MeO}$, $9_{PhO}$, $9_{Th}$, $1_F$, $1_{MeO}$, $1_{PhO}$, and $1_{Th}$ in Table 1 represent compounds in which each of r in Compound $8_r$, $9_r$, and $1_r$ is a phenyl group, a 3-fluorophenyl group, a 4-methoxyphenyl group, a 4-phenoxyphenyl group or a 3-thienyl group as represented below.

TABLE 1

| | Example 2 | Example 3 | Example 4 | Example 5 |
|---|---|---|---|---|
| | First step | | | |
| Reactant | Compound 7 | Compound 7 | Compound 7 | Compound 7 |
| | 5.0 g (18 mmol) | 1.8 g (6.3 mmol) | 1.2 g (4.3 mmol) | 2.2 g (7.9 mmol) |
| Reagent | (3-fluorophenylacetylene) | (4-methoxyphenylacetylene) | (4-phenoxyphenylacetylene) | (3-ethynylthiophene) |
| | 2.6 g (22 mmol) | 1.0 g (7.6 mmol) | 1.0 g (5.2 mmol) | 1.0 g (9.5 mmol) |
| Product | Compound $8_F$ | Compound $8_{MeO}$ | Compound $8_{PhO}$ | Compound $8_{Th}$ |
| | 4.5 g (14 mmol), 79% | 1.5 g (4.6 mmol), 72% | 0.74 g (1.9 mmol), 44% | 1.6 g (5.3 mmol), 67% |
| | Second Step | | | |
| Reactant | Compound $8_F$ | Compound $8_{MeO}$ | Compound $8_{PhO}$ | Compound $8_{Th}$ |
| | 1.0 g (3.2 mmol) | 1.0 g (3.1 mmol) | 0.7 g (1.8 mmol) | 1.5 g (5.0 mmol) |
| Reagent | HONH₂•HCl | HONH₂•HCl | HONH₂•HCl | HONH₂•HCl |
| | 0.66 g (9.5 mmol) | 0.42 g (6.1 mmol) | 0.37 g (5.4 mmol) | 1.4 g (20 mmol) |
| Product | Compound $9_F$ | Compound $9_{MeO}$ | Compound $9_{PhO}$ | Compound $9_{Th}$ |
| | 0.99 g (3.0 mmol), 95% | 1.0 g (2.9 mmol), 95% | 0.69 g (1.7 mmol), 95% | 1.6 g (5.0 mmol), 99% |
| | Third Step | | | |
| Reactant | Compound $9_F$ | Compound $9_{MeO}$ | Compound $9_{PhO}$ | Compound $9_{Th}$ |
| | 0.30 g (0.91 mmol) | 0.30 g (0.87 mmol) | 0.30 g (0.74 mmol) | 1.6 g (5.0 mmol) |

TABLE 1-continued

| | Example 2 | Example 3 | Example 4 | Example 5 |
|---|---|---|---|---|
| Reagent | $CF_3SO_2Cl$ 0.31 g (1.8 mmol) | $CF_3SO_2Cl$ 0.30 g (1.8 mmol) | $CF_3SO_2Cl$ 0.25 g (1.5 mmol) | $CF_3SO_2Cl$ 2.5 g (15 mmol) |
| Product | Compound $1_F$ 0.33 g (0.71 mmol), 79% | Compound $1_{MeO}$ 0.42 g (0.87 mmol), 99% | Compound $1_{PhO}$ 0.2 g (0.37 mmol), 50% | Compound $1_{Th}$ 1.6 g (3.5 mmol), 71% |

It was identified by analysis of $^1$H NMR and mass spectrometry below that the product obtained was Compound $1_F$. In addition, corresponding hydrogen atoms are represented in italics below.

$^1$H-NMR (400 MHz, $CDCl_3$): 7.169 (1H, ddd, J=6.2, 0.8 Hz, $C_6H_4F$—), 7.472-7.353 (3H, m, $C_6FH_4F$—), 7.925 (1H, t, J=7.8 Hz, —$C_{10}H_5$—), 8.021 (1H, d, J=8.0 Hz, —$C_{10}H_5$—), 8.641 (1H, d, J=7.6 Hz, —$C_{10}H_5$—), 8.730 (1H, dd, J=7.2, 1.2 Hz, —$C_{10}H_5$—), 8.831 (1H, dd, J=8.8, 1.2 Hz, —$C_{10}H_5$—). MS: 480.9 ([M+$NH_4$]$^+$).

It was identified by analysis of $^1$H NMR and mass spectrometry below that the product obtained was Compound $1_{MeO}$. In addition, corresponding hydrogen atoms are represented in italics below.

$^1$H-NMR (400 MHz, $CDCl_3$): 3.887 (3H, s, $CH_3O$—), 6.974 (2H, d, J=8.8 Hz, $CH_3OC_6H_4$—), 7.637 (2H, d, J=8.8 Hz, $CH_3OC_6H_4$—), 7.914 (1H, t, J=8.0 Hz, —$C_{10}H_5$—), 7.985 (1H, d, J=7.6 Hz, —$C_{10}H_5$—), 8.630 (1H, d, J=8.0 Hz, —$C_{10}H_5$—), 8.728 (1H, dd, J=7.2, 1.2 Hz, —$C_{10}H_5$—), 8.871 (1H, dd, J=8.0, 0.8 Hz, —$C_{10}H_5$—) MS: 492.9 ([M+$NH_4$]$^+$.

It was identified by analysis of $^1$H NMR and mass spectrometry below that the product obtained was Compound $1_{PhO}$. In addition, corresponding hydrogen atoms are represented in italics below.

$^1$H-NMR (400 MHz, Acetone-d6): 7.140-7.082 (1H, m, $C_6H_5$—), 7.237 (1H, t, J=7.2 Hz, $C_6H_5O$—), 7.483-7.443 (1H, m, —$C_6H_4$—), 7.656-7.634 (1H, m, —$C_6H_4$—), 7.754-7.731 (1H, m, —$C_6H_4$—), 7.815-7.786 (1H, m, —$C_6H_4$—), 8.080 (1H, t, J=8.0 Hz, —$C_{10}H_5$—), 8.151 (1H, d, J=7.6 Hz, —$C_{10}H_5$—), 8.654 (1H, d, J=7.6 Hz, —$C_{10}H_5$—), 8.734 (1H, dd, J=7.2, 1.2 Hz, —$C_{10}H_5$—), 9.004 (1H, dd, J=8.4, 1.2 Hz, —$C_{10}H_5$—). MS: 539.1 ([M+H]$^+$).

It was identified by analysis of $^1$H NMR and mass spectrometry below that the product obtained was Compound $1_{Th}$. In addition, corresponding hydrogen atoms are represented in italics below.

$^1$H-NMR (400 MHz, $CDCl_3$): 7.348 (1H, d, J=4.8 Hz, $C_4SH_3$—), 7.424 (1H, dd, J=4.8, 2.8 Hz, $C_4SH_3$—), 7.771 (1H, d, J=2.8 Hz, $C_4SH_3$—), 7.922 (1H, t, J=8.0 Hz, —$C_{10}H_5$—) 8.005 (1H, d, J=8.0 Hz, —$C_{10}H_5$—), 8.640 (1H, d, J=8.0 Hz, —$C_{10}H_5$—), 8.735 (1H, d, J=7.2 Hz, —$C_{10}H_5$—), 8.853 (1H, d, J=7.6 Hz, —$C_{10}H_5$—). MS: 452.1 ([M$^+$]).

Figure 2:
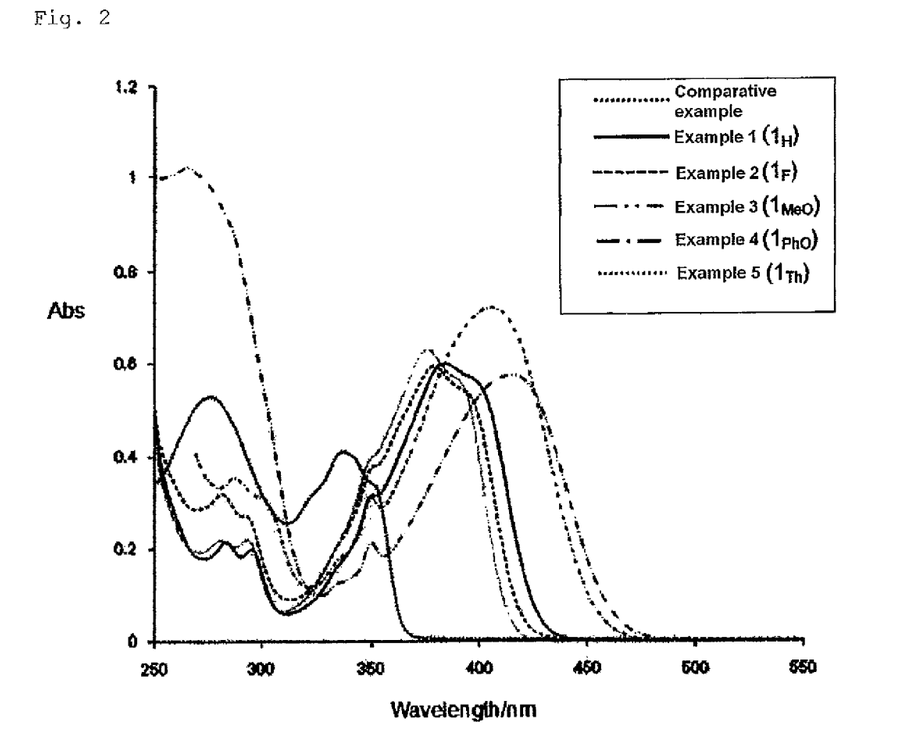
FIG. 2 is an absorption spectrum graph of compounds obtained in Examples 1 to 5.
Figure 3:
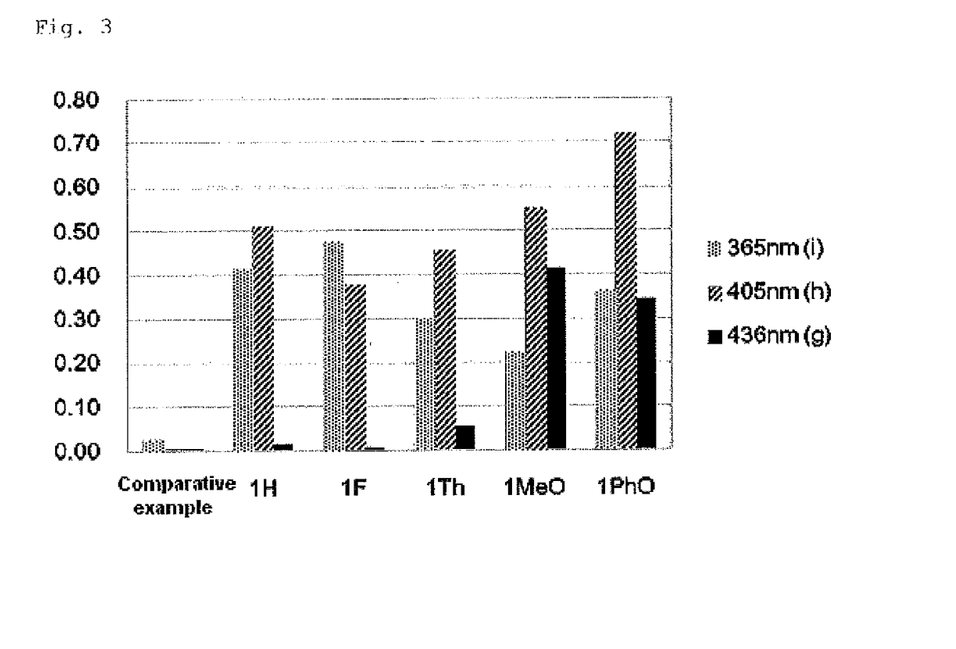
FIG. 3 is a graph showing absorbances for g-line, h-line and i-line of each compound obtained in Examples 1 to 5.

Absorption spectrums of compounds obtained in Examples 1 to 5 were measured. The results are shown in FIG. 2. The absorbances thereof in g-line, h-line, and i-line are as shown in Tables 3 and FIG. 3. Furthermore, N-trifluoromethanesulfonyloxy-1,8-naphthalimide was used as a comparative example.

TABLE 2

| Compound | 365 nm (i-line) | 405 nm (h-line) | 436 nm (g-line) |
|---|---|---|---|
| Comparative example | 0.02924852 | 0.00557481 | 0.00464166 |
| $1_H$ | 0.41618329 | 0.51116955 | 0.01498808 |
| $1_F$ | 0.47716007 | 0.38023609 | 0.00675271 |
| $1_{Th}$ | 0.29889166 | 0.45672727 | 0.05731016 |
| $1_{MeO}$ | 0.22617087 | 0.55094427 | 0.41525635 |
| $1_{PhO}$ | 0.36206427 | 0.71874785 | 0.34383583 |

It was measured and evaluated by devices and a method (Evaluation test of acid generating ability) described below whether compounds obtained in Examples above acted as an acid generator under photoirradiation. The actual evaluation was conducted by use of Compound $1_H$. Devices used in evaluation are as follows.

[1] Ultraviolet and visible absorption spectrum
Types of machines: Varian Cary4000 manufactured by Agilent Technologies, Inc.
Measurement solvent: Dichloromethane
[2] Hand-held UV lamp
Types of machines: SLUV-4 manufactured by AS ONE Corporation
Wavelength used: 365 nm
[Evaluation Method]
(1) 20 μL Compound $1_H$ solution in dichloromethane was prepared and a few drops of 50% bromocresolgreen (BCG) solution in ethanol were added in this solution as pH probe.
(2) The absorption spectrum of the solution was measured and it was checked that there are maximum absorption spectrums of Compound $1_H$ in 300-400 nm and BOG in 630 nm. The color of this solution was dark blue.
(3) The absorption spectrum of the solution was measured every 2 minutes while irradiating the solution described (2) above by UV lamp. At this time, the progress of attenuation concerning absorption maximum of BCG spectrum and the discoloration situation of dark blue color in the solution due to the pH decline of the system by generation of acids were observed by eyes.

Figure 4:
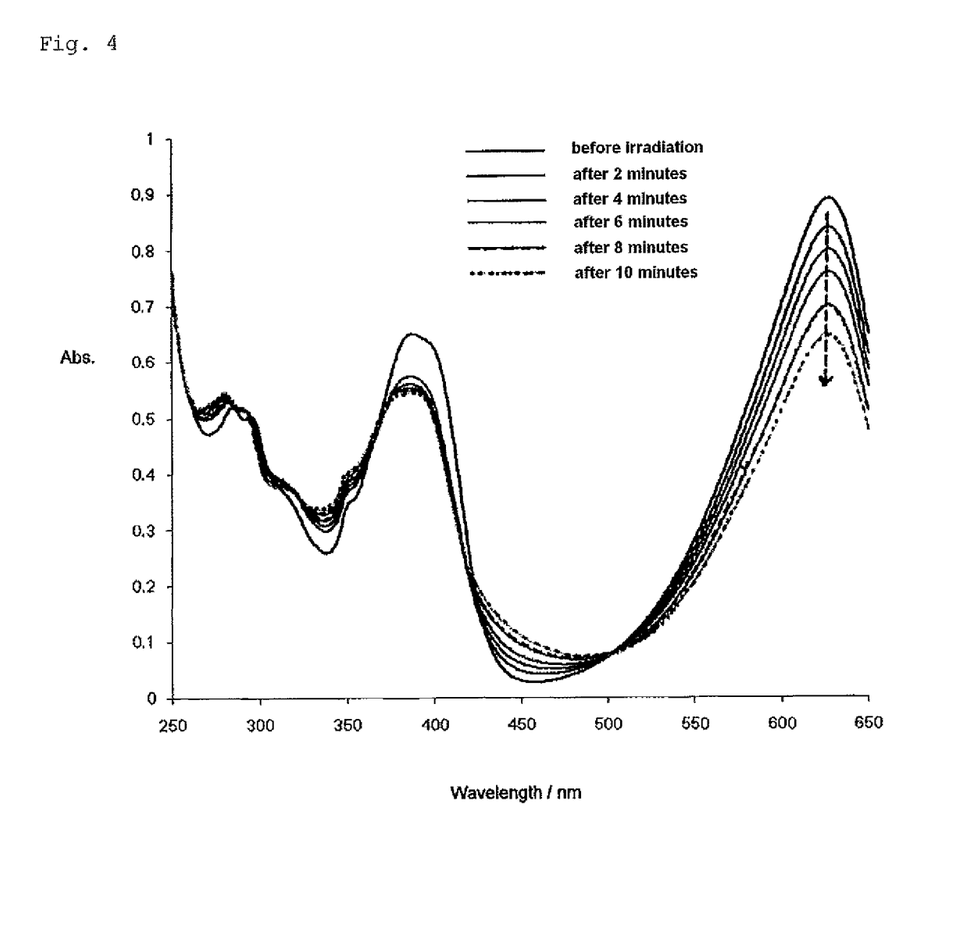
FIG. 4 is a graph showing the change with time of absorption spectrum when the compound obtained in Example 1 was irradiated by light.

The conditions of irradiation applied in Example above, that is, use of UV lamp as a light source and above-described wavelength as maximum threshold wavelength were determined from the view point of availability. The results are shown in FIG. 4.

Further, a photoresist composition I was prepared by use of Compound $1_H$. The photoresist consists of a terpolymer resin having polymerization units of hydroxystyrene, styrene, and tert-butylacrylate, tetrabutylammonium hydroxide (0.3 weight-% to the weight of the resin), m- and p-cresol novolak resin (33 weight-% to the weight of the resin), polypropylene glycol monobutyl ether (8.0 weight-% to the weight of the resin), polyvinyl ether (8.0 weight-% to the weight of the resin), a surfactant (0.12 weight-% to the total solids), Compound $1_H$ (1.5 weight-% to the weight of the resin), and solvent (propylene glycol-1-monomethyl ether-2-acetate).

In addition, a photoresist composition was prepared by the same manner as the above described photoresist composition except for using N-trifluoromethanesulfonyloxy-1,8-naphthalimide (manufactured by Toyo Gosei CO., Ltd.) instead of Compound $1_H$ as a comparative example for the above described photoresist composition.

Lithography tests of the photoresist composition using compound $1_H$ and the comparative example photoresist composition were conducted and the resist patterning efficiencies at a g- and h-line containing broadband exposure were evaluated. The devices and conduct conditions used in Example were as follows.

[1] Coater
Machine: DSW-636BPV manufactured by Dainippon Screen Mfg., Ltd.
[2] Exposure machine (Contact aligner)
Machine: MA-200/ML manufactured by SUSS MicroTec AG.
Light source: broadband light source
[3] Scanning electron microscope (SEM)
Types of machines: S-4700 manufactured by Hitachi, Ltd.
[Evaluation Method]
The photoresist was applied on a HMDS-processed silicon wafer and baked at 135° C. for 360 seconds to obtain a resist film with a film thickness of 50 micron. The wafer with the photoresist film was exposed with doses of 1200 mJ/cm$^2$ and 1500 mJ/cm$^2$ by using a contact hole pattern mask. The wafer was baked at 105° C. for 100 seconds and then developed for 210 seconds by a dip method with a AZ 300MIF developer (2.38% TMAH). The patterns formed on the wafer was observed by a scanning electron microscope and a hole size on the surface of the film was measured. In Table 3, the measuring results of hole size on 30 μm 1:1 contact hole pattern are shown. The unit of the hole size is μm.

TABLE 3

| | 1200 mJ/cm$^2$ | 1500 mJ/cm$^2$ |
|---|---|---|
| Comparative example | 34.5 | 34.5 |
| Composition I | 37.1 | 38.1 |

From the results of lithography test, the photoresist composition I recorded larger hole size patterns formation than the comparative photoresist composition in each exposure dose. Those results indicate that Compound $1_H$ contained in the photoresist composition I acts as a better acid generator when light of long wavelength side are contained in an exposure light source.

Embodiments described above are only exemplifications. All matters having the substantially same constitution as technical idea described in the claims and showing the same working-effect as the present invention are included in a technical scope of the present invention.

The invention claimed is:

1. An aromatic imide compound represented by the formula (1):

(1)

wherein in R$^1$ represents a haloalkyl group having 1 to 7 carbon atoms or a haloaryl group, R$^3$ represents a halogen atom or a hydrocarbon group n is zero or an integer of 1 or more, m is at least 1 and a sum of n and m is 1 to 6, and $R^2$ is the group $R^4$-$R^5$— wherein $R^4$ is selected from the group consisting of and where $R^5$ is an alkenylene group or an alkynylene group.

2. The aromatic imide compound according to claim 1, which can absorb light of g-line (436 nm) and/or h-line (405 nm) as measured using ultraviolet absorption spectroscopy of a solution of this aromatic imide compound in solution in methylene chloride, and where the addition of bromocresolgreen imparts a dark blue color to this solution, and further where upon irradiation with this light, the solution shows both a discoloration of the dark blue color indicating of a decreasing pH, and an attenuation of an absorption maximum measured by ultraviolet spectroscopy at the g-line (436 nm) and/or h-line (405 nm).

3. The aromatic imide compound represented by the formula (1) of claim 1 wherein $R^1$ represents a haloalkyl group having 1 to 7 carbon atoms.

4. The aromatic imide compound represented by the formula (1) of claim 3, where $R^5$ is an alkynylene group.

5. An aromatic imide compound represented by formula (2):

(2)

wherein, $R^1$ represents a haloalkyl group having 1 to 7 carbon atoms or a haloaryl group, $R^4$ is selected from the group consisting of 6. The aromatic imide compound of claim 5 wherein, $R^1$ represents a haloalkyl group having 1 to 7 carbon atoms.

7. The aromatic imide compound of claim 5 wherein, $R^1$ represents a haloalkyl group having 1 to 7 carbon atoms and $R^4$ is selected from the group consisting of 8. The aromatic imide compound of claim 5 wherein the haloalkyl group having 1 to 7 carbon atoms or the haloaryl in one where the halo moiety is a fluorine atom and further where, respectively, a part or all of hydrogen atoms in the alkyl group of the haloalkyl or the aryl of the haloaryl group are substituted by a fluorine atoms, and further where the alkyl group of the haloalkyl is selected from the group consisting of a linear alkyl, a branched alkyl and a cyclic alkyl groups.

9. The aromatic imide compound of claim 5 wherein the haloalkyl group having 1 to 7 carbon atoms or the haloaryl in one where the halo moiety is a fluorine atom and further where, respectively, a part or all of hydrogen atoms in the alkyl group of the haloalkyl or the aryl of the haloaryl group are substituted by a fluorine atoms, and further where the alkyl group of the haloalkyl is selected from the groups consisting of a methyl group, an ethyl group, a propyl group, a butyl group, a pentyl group, a hexyl group, and a heptyl group and further where the aryl group of the haloaryl is selected from phenyl or tolyl.

10. The aromatic imide compound of claim 5 wherein $R^1$ is a haloalkyl group having 1 to 7 carbon atoms, and this haloalkyl is in one where the halo moiety is a fluorine atom and further where a part or all of hydrogen atoms in the alkyl group of the haloalkyl are substituted by a fluorine atoms, and further where the alkyl group of the haloalkyl is selected from the groups consisting of a methyl group, an ethyl group, a propyl group, a butyl group, a pentyl group, a hexyl group, and a heptyl group.

11. The aromatic imide compound of claim 5 wherein the aromatic imide compound is selected from the compounds having structure ($1_{ra}$), (1ra)

and further wherein $R^1$ represents a haloalkyl group having 1 to 7 carbon atoms or a haloaryl group, and where $R^4$ is selected from the group consisting and where the haloalkyl or the haloaryl in one where the halo moiety is a fluorine atom and further where, respectively, a part or all of hydrogen atoms in the alkyl group of the haloalkyl or the aryl of the haloaryl group are substituted by a fluorine atoms.

12. The aromatic imide compound of claim 11 wherein the haloalkyl group having 1 to 7 carbon atoms, where the halo moiety is a fluorine atom and further where, respectively, a part or all of hydrogen atoms in the alkyl group of the haloalkyl or the aryl of the haloaryl group are substituted by a fluorine atoms and further where the alkyl group in the haloalkyl is selected from the groups consisting of a linear alkyl, a branched alkyl and a cyclic alkyl groups.

13. The aromatic imide compound of claim 11 wherein the haloalkyl group having 1 to 7 carbon atoms, where the halo moiety is a fluorine atom and further wherein, respectively, a part or all of hydrogen atoms in the alkyl group of the haloalkyl, or the aryl of the haloaryl group are substituted by a fluorine atoms and further where the alkyl group of the haloalkyl is selected from the groups consisting of a methyl group, an ethyl group, a propyl group, a butyl group, a pentyl group, a hexyl group, and a heptyl group and further where the aryl group of the haloaryl is selected from phenyl or tolyl.

14. The aromatic imide compound of claim 11 wherein $R^1$ is a haloalkyl group having 1 to 7 carbon atoms, where the halo moiety is a fluorine atom and further where, respectively, a part or all of hydrogen atoms in the alkyl group of the haloalkyl are substituted by a fluorine atom and further where the alkyl group of the haloalkyl is selected from the groups consisting of a methyl group, an ethyl group, a propyl group, a butyl group, a pentyl group, a hexyl group, and a heptyl group.

15. The aromatic imide compound of claim 14 wherein $R^4$ is selected from the group consisting of

* * * * *